United States Patent [19]

Noiles et al.

[11] 4,410,125
[45] Oct. 18, 1983

[54] SURGICAL STAPLER APPARATUS WITH CURVED STAPLE PUSHER

[75] Inventors: Douglas G. Noiles, New Canaan; David T. Green, Norwalk, both of Conn.

[73] Assignee: United States Surgical Corporation, Norwalk, Conn.

[21] Appl. No.: 308,183

[22] Filed: Oct. 2, 1981

[51] Int. Cl.³ .............................................. A61B 17/10
[52] U.S. Cl. ..................................... 227/19; 227/145; 227/DIG. 1; 128/334 R
[58] Field of Search .................. 72/409, 410; 128/325, 128/326, 334 R; 227/19, DIG. 1, 83, 107, 129, 139, 143, 144, 145

[56] References Cited

U.S. PATENT DOCUMENTS

| | | | |
|---|---|---|---|
| 1,199,653 | 9/1916 | Bacolini | 227/DIG. 1 |
| 1,203,270 | 10/1916 | Richter | 227/DIG. 1 |
| 1,977,282 | 10/1934 | Kruse | 128/338 |
| 2,277,139 | 3/1942 | Niemand | 227/DIG. 1 |
| 2,678,443 | 5/1954 | Lindstrom | 227/DIG. 1 |
| 2,707,783 | 5/1955 | Sullivan | 227/DIG. 1 |
| 3,160,890 | 12/1964 | Lefebvre | 227/DIG. 1 |
| 3,489,330 | 1/1970 | Mallina et al. | 227/19 |
| 3,807,407 | 4/1974 | Schweizer | 128/334 R |
| 3,873,016 | 3/1975 | Fishbein | 227/83 |
| 4,109,844 | 8/1978 | Becht | 227/120 |
| 4,127,227 | 11/1978 | Green | 227/83 |
| 4,164,225 | 8/1979 | Johnson et al. | 128/334 R |
| 4,166,466 | 9/1979 | Jarvik | 128/325 |
| 4,179,057 | 12/1979 | Becht et al. | 227/19 |
| 4,185,762 | 1/1980 | Froehlich | 227/138 |
| 4,202,480 | 5/1980 | Annett | 227/8 |
| 4,204,623 | 5/1980 | Green | 227/19 |
| 4,241,861 | 12/1980 | Fleischer | 227/135 |
| 4,256,251 | 3/1981 | Moshofsky | 227/120 |
| 4,261,244 | 4/1981 | Becht et al. | 411/472 |
| 4,296,751 | 10/1981 | Blake et al. | 128/325 |
| 4,316,468 | 2/1982 | Klieman et al. | 128/325 |

FOREIGN PATENT DOCUMENTS

| | | |
|---|---|---|
| 1082552 | 7/1980 | Canada . |
| 40683 | 12/1981 | European Pat. Off. . |
| 1082552 | 7/1980 | Canada . |

*Primary Examiner*—Paul A. Bell
*Attorney, Agent, or Firm*—Robert R. Jackson; John E. Nathan

[57] ABSTRACT

Surgical stapler apparatus of the type in which a surgical staple is formed around an anvil. The staple is driven by a longitudinally curved pusher which forms an arc of a circle and which is arcuately reciprocal in a similarly curved channel. The distal end portion of the curved channel is substantially tangent to the plane of the distal-most staple in a stack of staples, and the proximal end portion of the staple pusher is substantially parallel to the longitudinal axis of the stack to provide a very compact stapler configuration.

14 Claims, 20 Drawing Figures

SURGICAL STAPLER APPARATUS WITH CURVED STAPLE PUSHER

BACKGROUND OF THE INVENTION

This invention relates to surgical staplers, and more particularly to surgical staplers of the type which are most frequently used for closing wounds in skin and fascia tissue.

Surgical staplers for closing wounds in skin and fascia tissue are well known (see, for example, Green U.S. Pat. No. 4,204,623). Generally in surgical staplers of this type, the entire stapler is external to the tissue at all times. The staples are applied singly in succession by being bent or formed around an anvil so that the opposite ends of the staple enter the tissue on respective opposite sides of the wound and draw the two sides of the wound together as the staple is formed around the anvil.

In many applications of staplers of this type it is desirable to have the hand of the operator which is holding and actuating the stapler as close as possible to the point at which the staple is to be applied. This increases the operator's accuracy in placing the staples. By the same token, however, the operator's hand and the instrument should not obstruct the operator's view of the stapling site any more than is absolutely necessary during application of the staple.

Another consideration which may influence the design of surgical staplers of this type is the increasing interest in disposable surgical instruments (i.e., surgical instruments which are inexpensive enough to be economically disposable after use in a single surgical procedure, thereby avoiding all difficulty and expense of cleaning and sterilizing the apparatus between uses). To be economically disposable, a surgical stapler is preferably made as small and as simply as possible, making the greatest possible use of inexpensive materials such as plastics and using the lightest possible construction.

In view of the foregoing, it is an object of this invention to improve and simplify surgical staplers of the type which are commonly used for closing wounds in skin and fascia.

It is a more particular object of this invention to provide improved skin and fascia surgical staplers in which the operator's hand is relatively close to the stapling site and in which the operator's view of the stapling site is obstructed as little as possible by either the stapler or the hand.

SUMMARY OF THE INVENTION

These and other objects of the invention are accomplished in accordance with the principles of the invention by providing a surgical stapler which is held at an angle to the surface of the tissue to be stapled. The staples are stored in the instrument in a longitudinal stack which is substantially parallel to the longitudinal axis of the instrument. The staples are inclined relative to the longitudinal axis of the stack so that the plane of each staple is substantially perpendicular to the surface of the tissue to be stapled. The distal-most staple in the stack is applied to the tissue by being bent or formed around an anvil near that staple. The staple is formed around the anvil by a longitudinally curved staple pusher which extends in an arc of a circle from a plane tangent to the distal-most staple to a plane substantially parallel to, but laterally spaced from, the longitudinal axis of the stack of staples. An actuator adjacent the proximal end of the staple pusher reciprocates the pusher along its arc of curvature so that the distal end of the pusher advances the distal-most staple to the anvil and forms the staple around the anvil.

The design of the stapler is extremely compact. Adjacent the distal end of the apparatus the curved staple pusher converges toward the stack of staples so that the distal portion of the apparatus can be made relatively small and streamlined with no outward protrusions to unnecessarily obstruct the operator's view of the stapling site. Visibility of the stapling site is also enhanced by the fact that the instrument is held at an angle to the surface of the tissue. Because the staple pusher curves to intersect the distal end of the staple stack, there is no need for any complicated staple feeding motions or any complicated linkages between the actuator elements and the staple pusher. This greatly simplifies the apparatus of this invention as compared to prior apparatus of the same general type.

Further features of the invention, its nature and various advantages will be more apparent from the accompanying drawing and the following detailed description of the invention.

BRIEF DESCRIPTION OF THE DRAWING

FIG. 15 shows a further stage in the operating cycle.

FIG. 17 is taken along the line 17—17 in FIG. 19.

DETAILED DESCRIPTION OF THE INVENTION

Although the invention is also applicable to surgical staplers which are permanent and which can therefore be reloaded with staples when the initial staple supply is exhausted, the invention will be fully understood from an explanation of its application to disposable surgical staplers. These are surgical staplers which are not intended to be reloaded and which are therefore discarded after use in a single surgical procedure or after the initial supply of staples is exhausted.

As shown in FIGS. 1-15, a first illustrative embodiment 10 of the invention includes a main body 20 comprising a number of body parts 22, 24, 26, and 28. Central body part 22 (FIGS. 2 and 5) forms the core of the apparatus on which the other parts are mounted. Top cover 24 (shown separately in FIG. 2) covers the upper portion of the apparatus and is attached to central body part 22 along the outer periphery of the apparatus. Bottom cover 26 (shown separately in FIG. 5) is similarly attached to central body part 22 and covers the lower portion of the apparatus. Rear cover 28 (also shown separately in FIG. 5) is a proximal extension of bottom cover 26 which extends from the proximal end of bottom cover 26 to the proximal end of central body part 22. All of body parts 22, 24, 26, and 28 may be made of plastic and may be permanently joined together by interlocking tabs, adhesive, or any similar means.

The distal end portion of stapler 10 includes exterior surface portions 27 which are inclined by an acute angle A (FIG. 12) relative to the longitudinal axis 12 of the apparatus. In use, stapler 10 is held with external surface portions 27 either flush with the surface of the tissue 14 to be stapled or very close to and substantially parallel to the tissue surface. Accordingly, the longitudinal axis 12 of the instrument forms an acute angle A with the tissue surface during use of the stapler. Although angle A may depend on the intended application of the stapler, angle A is typically in the range from 30° to 60°, most preferably about 45° as in the particular embodiment shown in the drawing.

Figure 5:
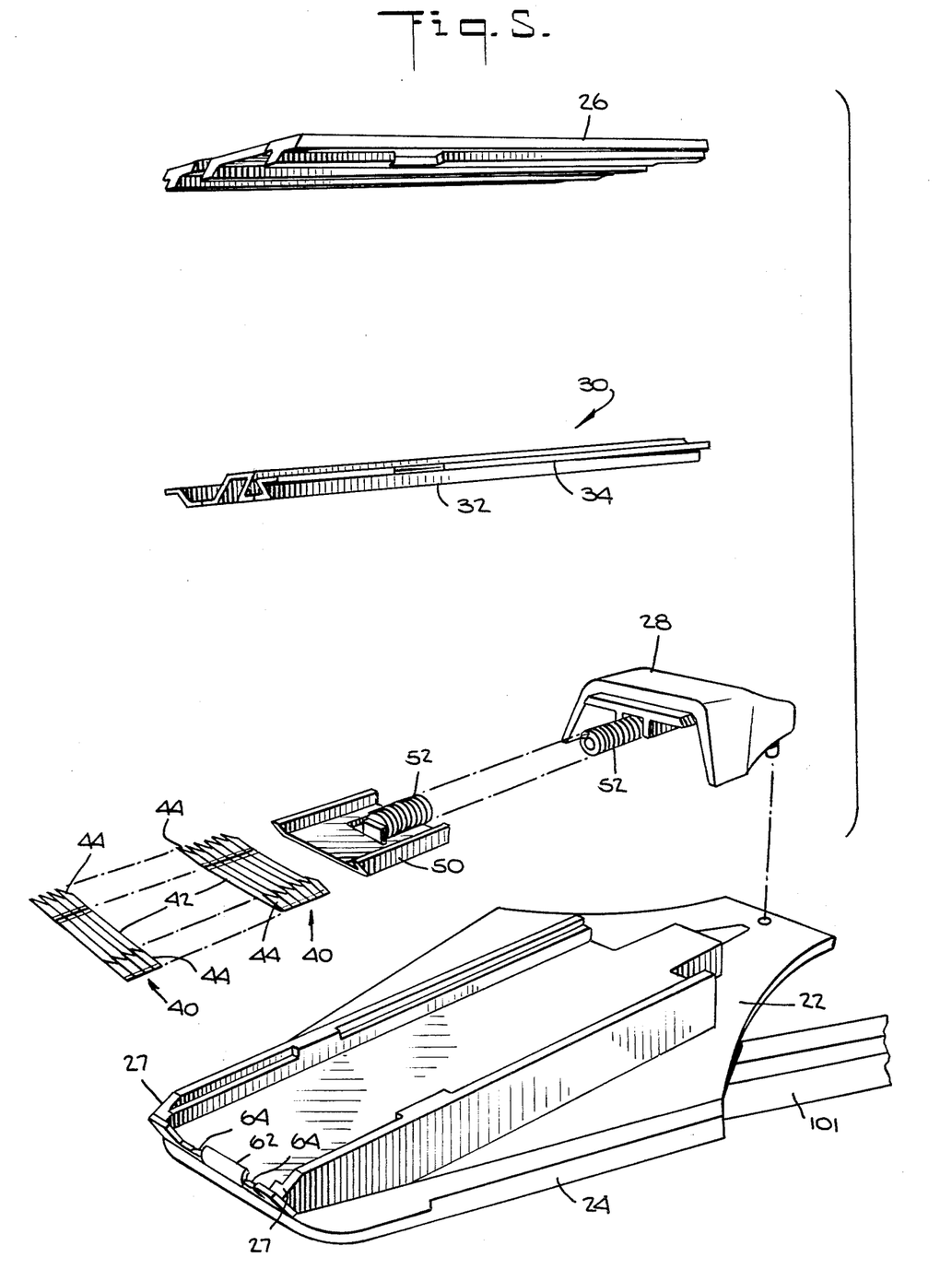
FIG. 5 is an exploded perspective view of the underside of the distal portion of the apparatus of FIGS. 1-4.
Figure 12:
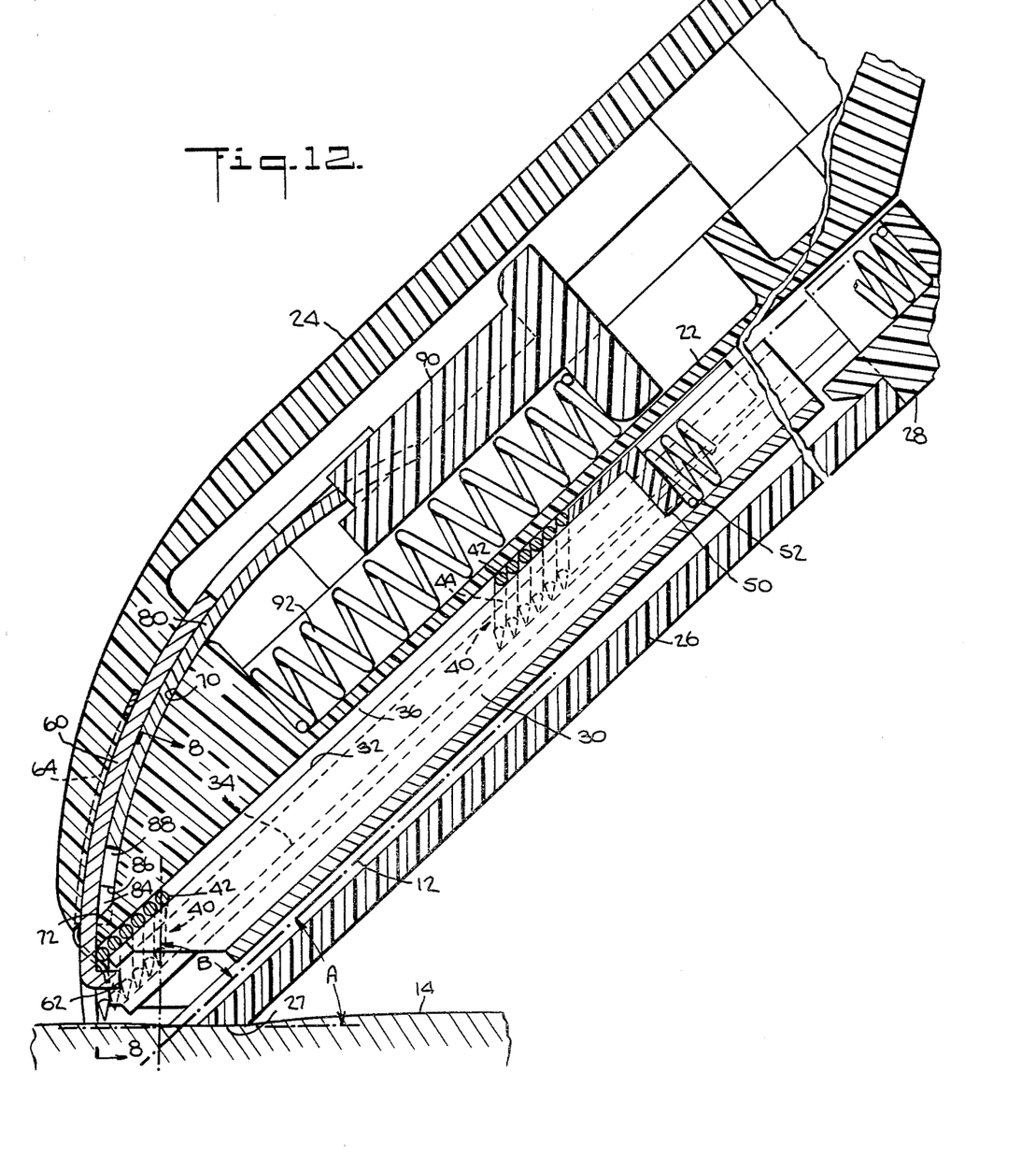
FIG. 12 is a partial longitudinal sectional view taken along the line 12—12 in FIG. 8.

As is best seen in FIGS. 5 and 12, inside bottom cover 26 is a longitudinally straight metal staple track 30 on which a plurality of U-shaped metal surgical staples 40 is slidably mounted in a longitudinal stack. The longitudinal axis of staple track 30 (and therefore the longitudinal axis of the stack of staples on track 30) is substantially parallel to the longitudinal axis 12 of the stapler. Each of staples 40 is preformed in a broadbased U shape having a crown portion 42 and two substantially parallel legs 44 at right angles to the crown at the respective opposite ends thereof. The free end of each staple leg is sharply pointed to facilitate entry of the staple into the tissue during stapling. The legs and crown of each staple lie in a plane which is referred to as the plane of the staple. Staples 40 are inclined relative to the longitudinal axis of the stapler so that when the stapler is held at the proper angle relative to the surface of the tissue to be stapled, the legs of the staples are substantially perpendicular to the tissue surface with the sharply pointed free ends of the staple legs pointing toward the tissue. Accordingly, the acute angle B (FIG. 12) between the plane of each staple and the longitudinal axis of the stack of staples is approximately equal to 90° minus angle A. Angle B is therefore typically in the range from 30° to 60°, most preferably about 45° as in the particular embodiment shown in the drawing.

Track 30 and central body part 22 cooperate to form a staple holding channel 36 (FIG. 12) in the body of the apparatus. The clearance between the upper surface 32 of track 30 and the opposite lower surface of main body part 22 is just large enough to allow the crowns 42 of staples 40 to move freely along the track. Staples 40 are maintained in the desired inclined position by (1) the inclined distal end of staple follower 50 (FIG. 5) adjacent the legs of the proximal-most staple, (2) the inclined distal end portion of pusher guide plate 60 (FIG. 12) adjacent the legs of the distal-most staple, and (3) the distance between the lower surface of central body part 22 and the surfaces 34 (FIGS. 5 and 12) of staple track 30 on which the free ends of staple legs 44 rest.

Staples 40 are maintained in abutting relationship and are resiliently urged in the distal direction along staple track 30 by staple follower 50 and compression coil spring 52 (FIGS. 5 and 12) which extends between staple follower 50 and an interior surface of rear cover 28.

The upper surface of the distal portion of central body part 22 includes a channel 70 (FIGS. 3 and 7) which is longitudinally curved in an arc of a circle. The distal end portion of channel 70 intersects and communicates with the distal end portion of staple holding channel 36. At the intersection between channels 36 and 70, the longitudinal axis of channel 70 is substantially tangent to the plane of the distal-most staple in the staple stack. The distal end portion of channel 70 also communicates with the exterior of the apparatus adjacent exterior surface portions 27, and the longitudinal axis of this portion of channel 70 is substantially perpendicular to the plane of surface portions 27. The proximal portion of channel 70 curves toward staple holding channel 36, until at its proximal end the longitudinal axis of channel 70 is substantially parallel to the longitudinal axis of channel 36.

Channel 70 is covered by longitudinally curved pusher guide plate 60 (FIGS. 3 and 12) which is typically made of metal. Pusher guide plate 60 forms an arc of a circle which conforms to the circular arc of channel 70. The distal end portion of pusher guide plate 60 is opposite the distal end of staple holding channel 36 and therefore constitutes a stop for the distal-most staple in the stack of staples in the staple holding channel. The central part of the distal end portion of pusher guide plate 60 is formed or bent inwardly to form anvil 62 (FIGS. 3 and 12) which is transverse to channel 70 at a location distal of the crown of the distal-most staple in the staple stack. Anvil 62 is cantilevered from pusher guide plate 60.

Figures 2, 3:
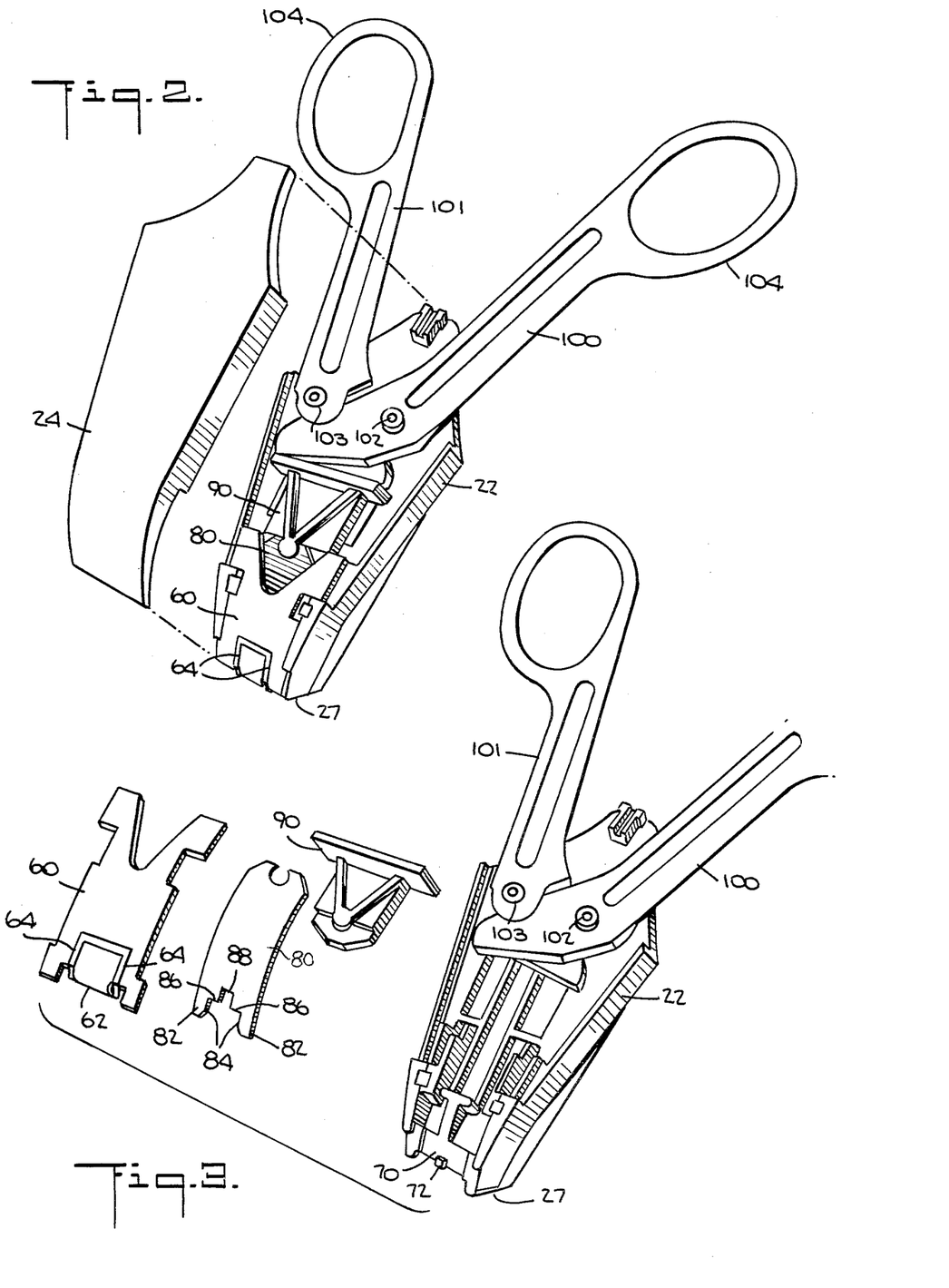
FIG. 2 is a view similar to FIG. 1 with a portion of the top cover removed to reveal the interior of the apparatus.
FIG. 3 is a view similar to FIG. 2 with additional parts removed to reveal additional details of the interior of the apparatus.
Figure 4:
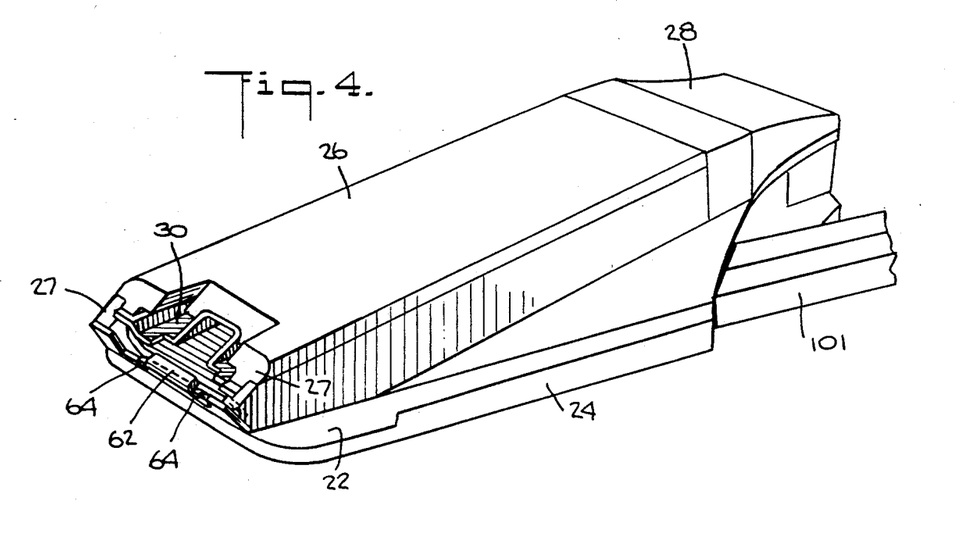
FIG. 4 is a partial perspective view of the underside of the distal portion of the apparatus of FIGS. 1-3.

Inside channel 70 is a longitudinally curved metal staple pusher 80 (FIGS. 3 and 12). Staple pusher 80 forms an arc of a circle which conforms to the circular arc of channel 70. Staple pusher 80 is preferably substantially rigid or inflexible and is arcuately reciprocal in channel 70. Before the apparatus is actuated as described in detail below, the distal end portion of staple pusher 80 is adjacent the crown 42 of the distal-most staple in the staple stack (see FIGS. 6, 7, 8, and 12). As can be seen, for example, in FIGS. 3 and 8, the distal end portion of staple pusher 80 includes two laterally spaced, distally extending fingers 82 separated by a longitudinal slot 84. The lateral dimension C of anvil 62 is substantially less than the length of the crown of a staple. The width D of slot 84 is less than the length of the staple crown, but greater than the dimension C of anvil 62. Accordingly, when staple pusher 80 is reciprocated toward the distal-most staple as shown progressively in FIGS. 9-11, the distal ends of fingers 82 respectively contact end portions 42a and 42b of staple crown 42 and bend those portions of the crown around anvil 62. The remaining central portion of staple crown 42 and anvil 62 enter slot 84. As can be seen in FIGS. 12-15, the distal end of staple track 30 is spaced from the distal end portion of staple guide plate 60 by a distance sufficient to allow only the distal-most staple to leave the staple stack and be bent around anvil 62 as described above. The thickness of at least the distal end portion of staple pusher 80 is sufficiently small to allow that portion of the staple pusher to pass between the distal end of track 30 and the opposite portion of staple guide plate 60.

Figure 7:
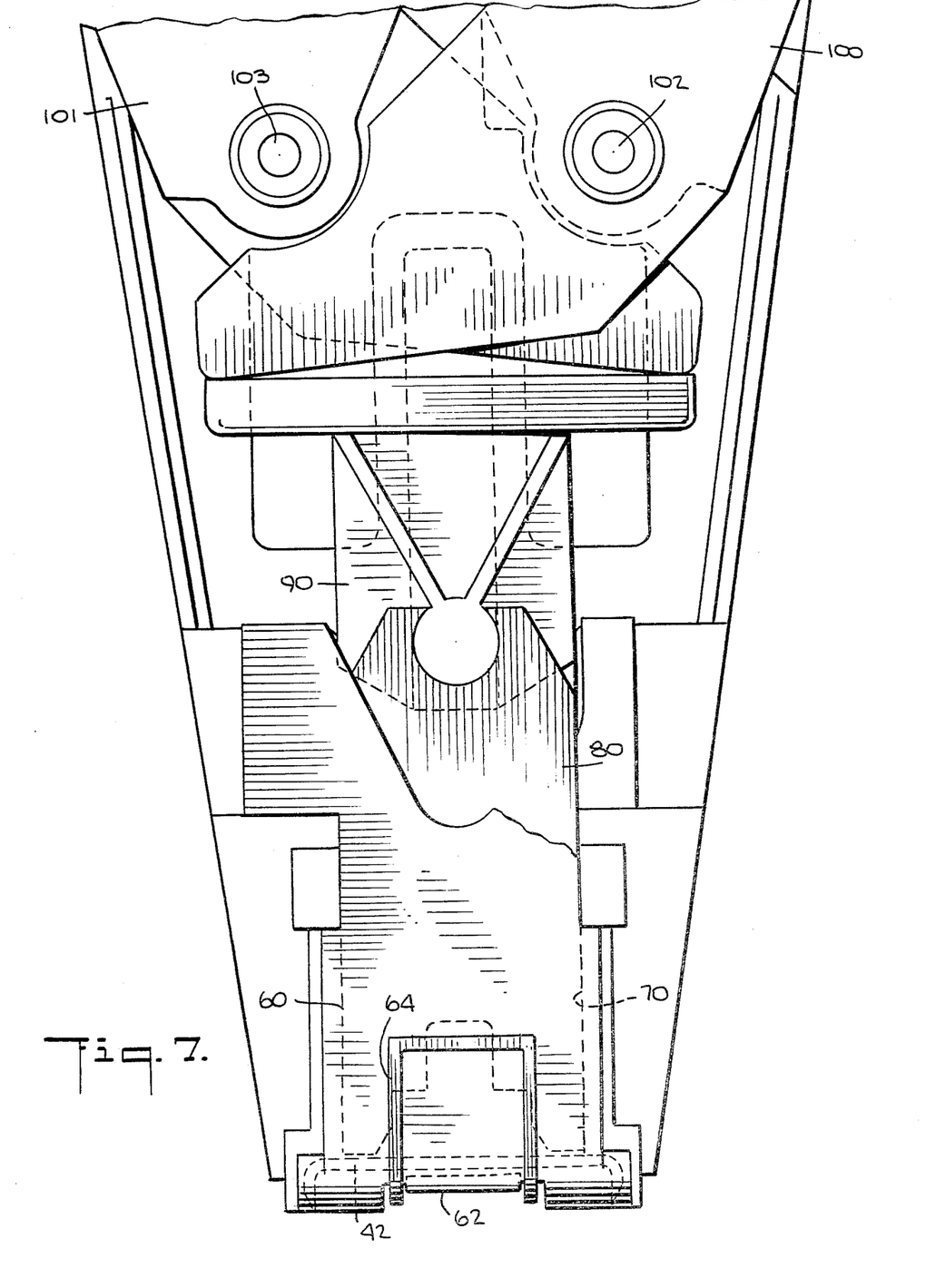
FIG. 7 is a top plan view of the distal portion of the apparatus of FIGS. 1-6 with a portion of the top cover cut away and showing the apparatus prior to commencement of an operating cycle.

As can be seen in FIGS. 2 and 7, the proximal end portion of staple pusher 80, which is substantially parallel to but laterally spaced from the longitudinal axis of the stack of staples, is connected to actuator element 90. Actuator element 90 is mounted for longitudinal reciprocal motion inside the body of the apparatus. Compression coil spring 92 (FIG. 12), which acts between an interior surface of the body and actuator element 90, resiliently biases element 90 in the proximal direction. Because staple pusher 80 is connected to actuator element 90, the staple pusher is also resiliently biased in the proximal direction.

Figure 1:
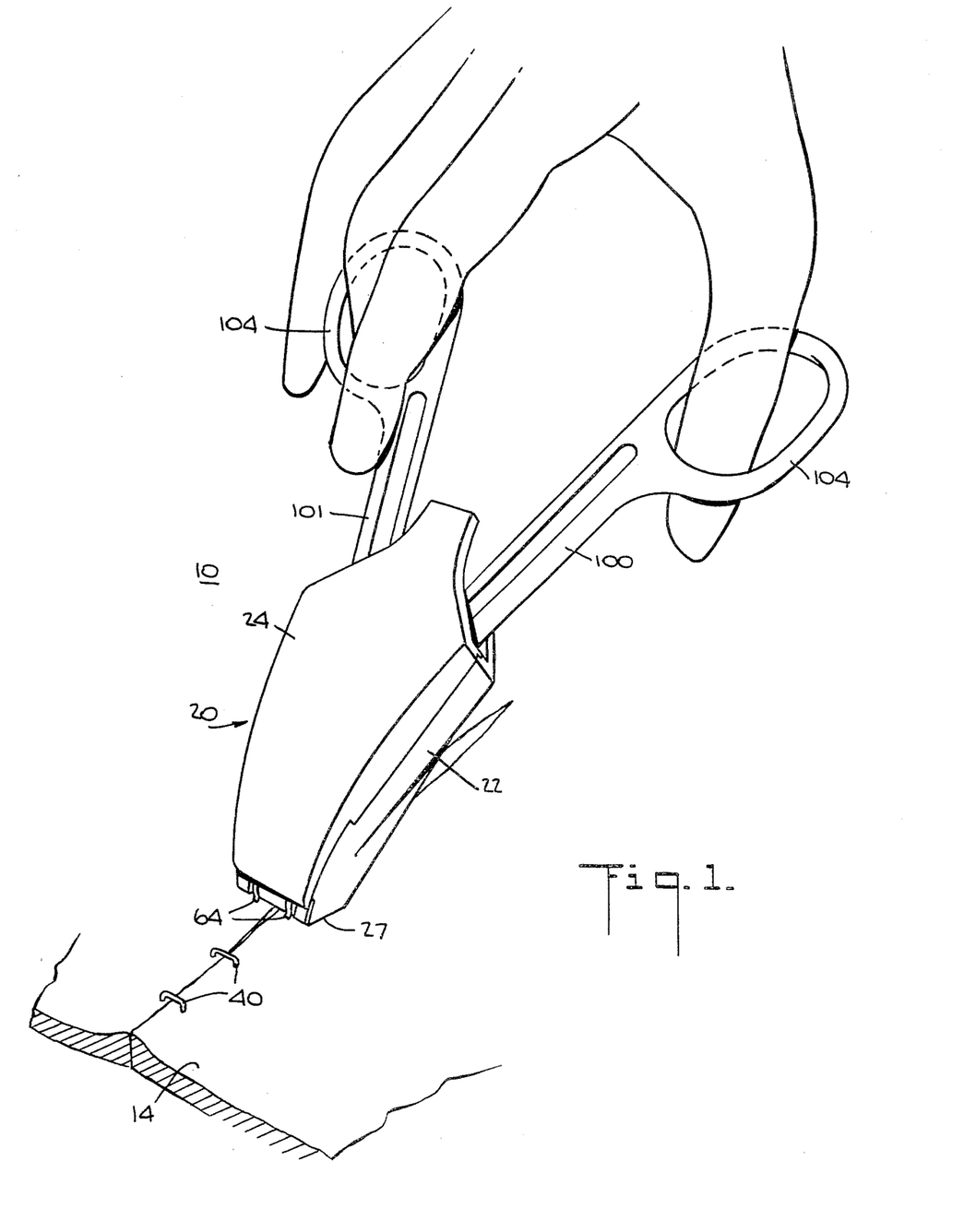
FIG. 1 is a perspective view of a first illustrative embodiment of the invention showing the apparatus in use.

On the proximal side of actuator element 90, ring handles 100 and 101 (FIGS. 1-3) are respectively pivotally mounted on the body of the apparatus by means of laterally spaced pivotal mountings 102 and 103. The pivotal axes of ring handles 100 and 101 are substantially parallel to one another and to a plane perpendicular to the longitudinal axis of the stack of staples. Ring handles 100 and 101 are disposed and operate in a plane which is tangent to the proximal end of staple pusher 80. Ring handles 100 and 101 include proximal finger rings 104 which, as shown in FIG. 1, are sized and spaced to accept the thumb and a finger of one hand of the operator of the apparatus. Distal surface portions of ring handles 100 and 101 contact the proximal surface of actuator element 90 so that when the ring handles are squeezed together, actuator element 90, and therefore staple pusher 80, translate in the distal direction. Ring handles 100 and 101 are resiliently biased apart as a result of the proximal bias of actuator element 90 produced by spring 92.

Figures 8, 9, 10, 11:
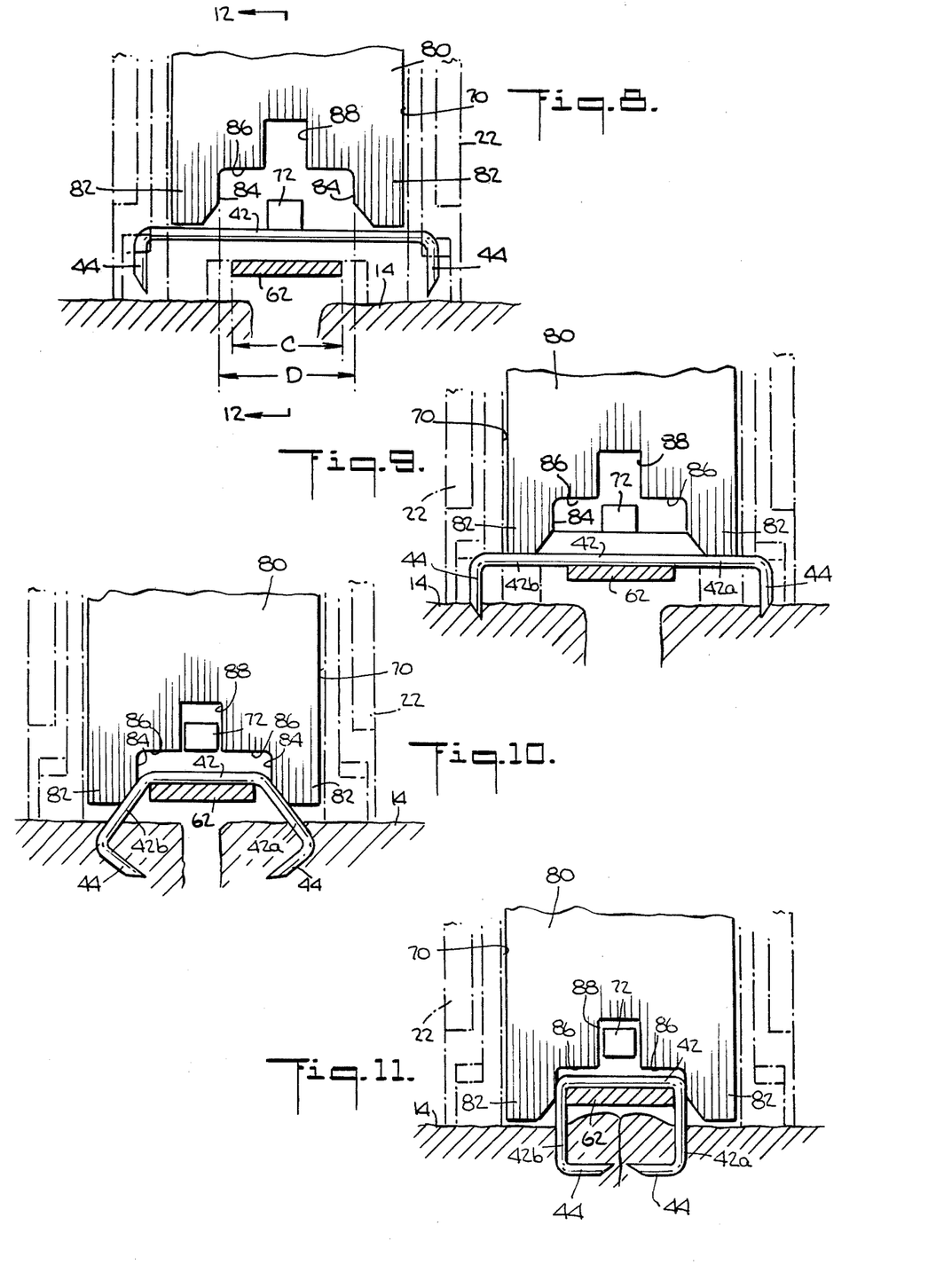
FIG. 8 is a partial sectional view of the apparatus of FIGS. 1-7 taken in the plane of the distal-most staple in the apparatus (i.e., along the line 8—8 in FIG. 12) and showing the apparatus prior to the commencement of an operating cycle.
FIGS. 9-11 are views similar to FIG. 8 which show successive stages in the operating cycle of the apparatus.

In use, the operator holds the apparatus by passing a thumb and one finger of one hand through finger rings 104 as shown in FIG. 1. The apparatus is positioned with distal end surface portion 27 flush with or substantially parallel to and closely adjacent the surface of the tissue to be stapled. The apparatus is located as shown in FIG. 8 so that each leg 44 of the distal-most staple is adjacent tissue 14 on a respective one of the opposite sides of the wound to be closed.

Figures 13, 14, 15:
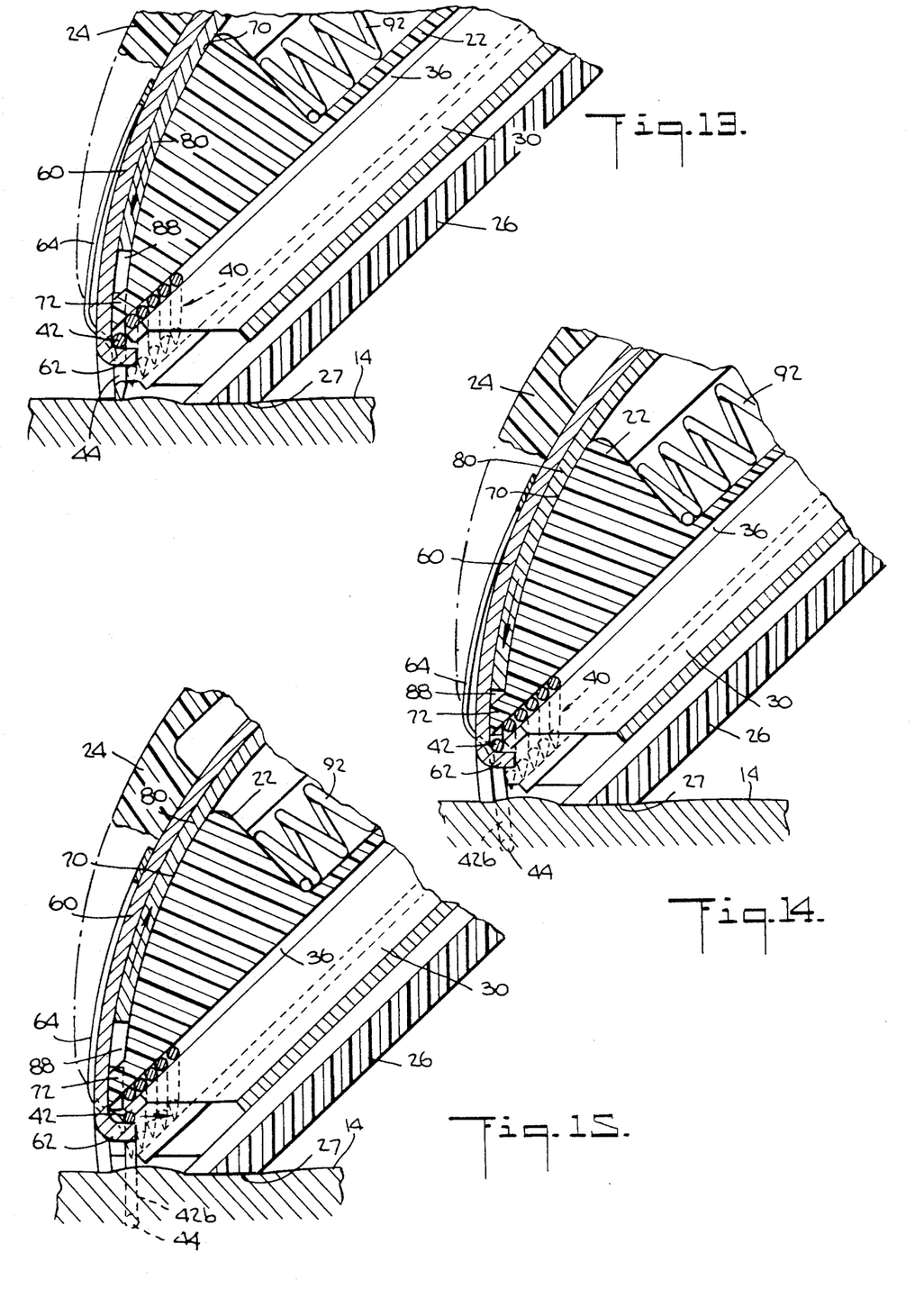
FIGS. 13-15 are views similar to FIG. 12 which show successive stages in the operating cycle of the apparatus. The stage in the operating cycle shown in FIG. 13 corresponds to the stage shown in FIG. 9; the stage shown in FIG. 14 corresponds to the stage shown in FIG. 11.

When it is desired to apply a staple, finger rings 104 are squeezed together. This causes actuator member 90 to translate in the distal direction, thereby causing staple pusher 80 to travel arcuately in the distal direction in channel 70 as shown progressively in FIGS. 9-11 and also in FIGS. 13 and 14. The distal ends of pusher fingers 82 contact the end portions 42a and 42b of the crown 42 of the distal-most staple in the staple stack. The distal-most staple leaves the staple stack and translates distally a short distance toward anvil 62 (FIGS. 9 and 14). The sharply pointed free ends of the distal-most staple emerge from the distal end of the apparatus and enter the tissue on opposite sides of the wound to be closed.

After a very short distal travel of the staple, the central portion of staple crown 42 contacts anvil 62. This prevents any further distal motion of this portion of the staple crown. Thereafter, continued distal motion of staple pusher 80 causes pusher fingers 82 to bend the end portions 42a and 42b of the staple crown around the lateral sides of anvil 62 (FIG. 10). This causes staple legs 44 to further penetrate the tissue and to be gradually redirected until they point toward one another inside the tissue (FIGS. 11 and 14). The adjacent portions of crown 42 also enter the tissue, and as these portions of the crown become parallel to one another, they tend to pull the two sides of the wound together. The distal motion of staple pusher 80 stops when shoulders 86 (FIG. 11) in slot 84 contact the central portion of crown 42 on anvil 62. The staple is shown fully formed in FIG. 11.

During the forming of the distal-most staple as described above, the presence of the distal end of staple pusher 80 between the distal end of staple track 30 and pusher guide plate 60 prevents the staple track from advancing in response to the urging of spring 52. When the staple has been fully formed, the squeezing pressure on ring handles 100 and 101 is released and elements 80, 90, 100, and 101 return to their initial positions in response to spring 92. When the staple which has just been formed is released from the pressure of staple pusher 80, staple ejection springs 64 (FIGS. 3, 7, and 15) on pusher guide plate 60 push the formed staple off anvil 62 as shown in FIG. 15, thereby facilitating removal of the stapler from the formed staple.

If for any reason the formed staple does not readily release from pusher slot 84, a narrow projection 72 (FIGS. 3, 6, 8, and 15), which extends from main body part 22 across the middle of channel 70 opposite anvil 62, acts as a backstop for the staple. Backstop 72 prevents the staple from being pulled any farther back into the apparatus than the initial position of the staple crown. This prevents the staple from jamming in the apparatus and from possibly injuring the stapled tissue by squeezing it between staple legs 44 and anvil 62. Staple pusher slot 84 has a portion 88 (FIG. 8) extending proximally between shoulders 86 so that backstop 72 does not interfere with the distal motion of staple pusher 80. Alternatively or in addition, staples with transverse surfaces as shown in Noiles et al. U.S. patent application Ser. No. 181,092, filed Aug. 25, 1980 may be used to prevent the staples from being pulled back into the apparatus when staple pusher 80 is retracted. (Nothing contained in the abovementioned Noiles et al. application is necessary to an understanding of the present invention, and it is referred to only to show a possible alternative or addition to what is shown and described herein.)

When staple pusher 80 has retracted in the proximal direction and the staple which has just been formed is out of the instrument, spring 52 urges the stack of staples in the distal direction until the next staple in the stack comes to rest against the distal portion of pusher guide plate 60. The apparatus is now ready to apply another staple when ring handles 100 and 101 are squeezed together again.

FIGS. 16-20 show a second illustrative embodiment 110 of the invention which is basically similar to the first embodiment but which has a different type of actuator. Instead of ring handles movable in a plane perpendicular to a plane perpendicular to the longitudinal axis of the staple stack, stapler 110 has a single trigger 120 pivotable about an axis parallel to a plane perpendicular to the longitudinal axis of the stack of staples. Except for this difference in the actuator mechanism, stapler 110 may be substantially the same as stapler 10. Accordingly, the same reference numbers are applied to similar or identical parts in staplers 10 and 110, and parts which have already been described in relation to stapler 10 will not be described in detail again in relation to stapler 110.

Figures 16, 17:
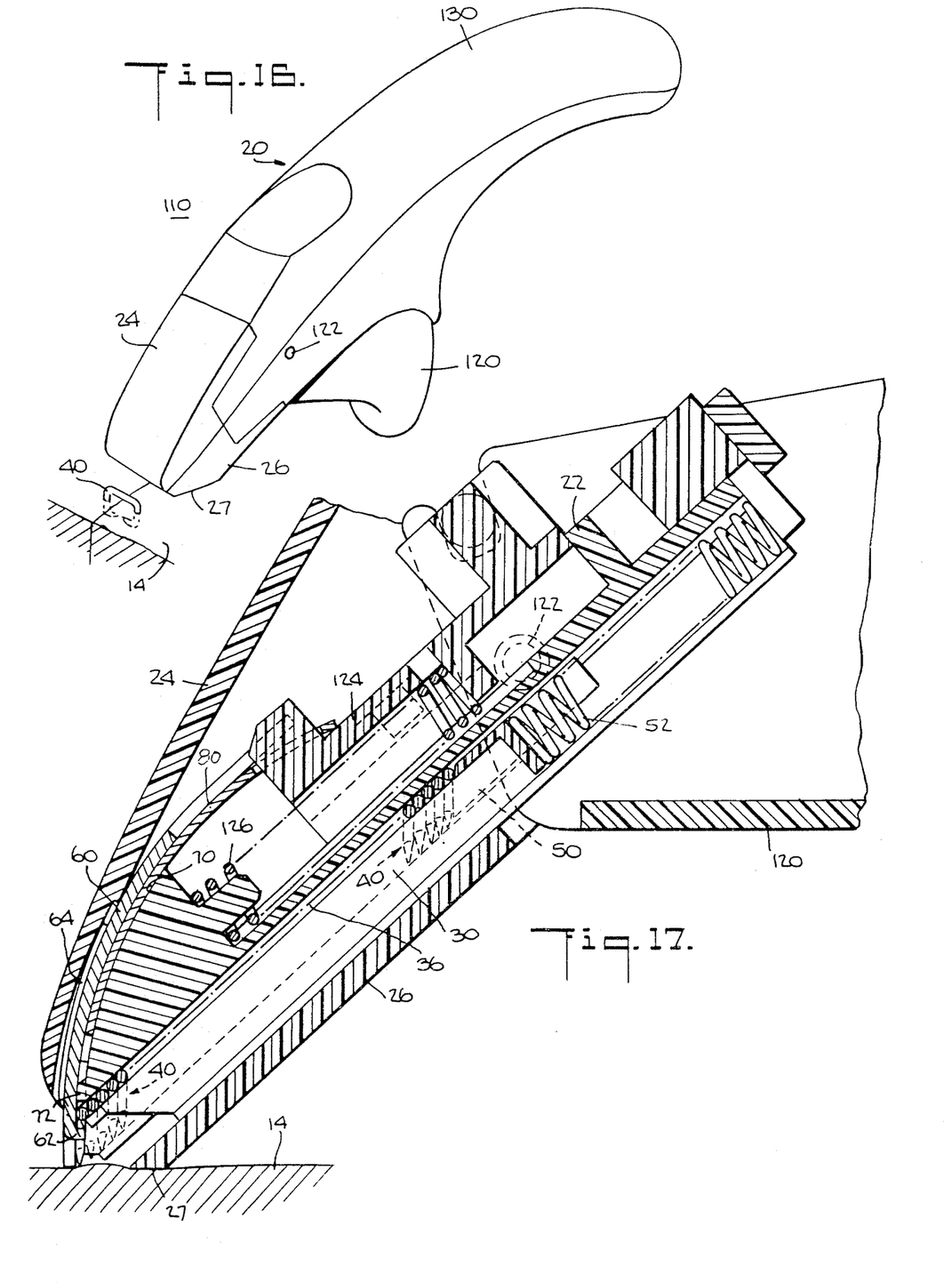
FIG. 16 is a perspective view of a second illustrative embodiment of the invention.
FIG. 17 is a longitudinal sectional view of the distal portion of the apparatus of FIG. 6 showing the apparatus prior to the commencement of an operating cycle.

The main body 20 of stapler 110 is made up of central body part 22, top cover 24, bottom cover 26, and proximally extending portion 130. Proximally extending portion 130 is sized and shaped to fit comfortably in the palm of the operator's hand, with trigger 120 being within reach of one or more fingers of that hand. Trigger 120 is pivotally mounted on main body 20 by means of pivotal axis 122. Pivotal axis 122 is substantially parallel to a plane which is perpendicular to the longitudinal axis of the stack of staples 40.

Staple track 30 forms a longitudinal staple holding channel 36 with the adjacent lower surface of central body part 22. A longitudinal stack of inclined staples 40 is present in the staple holding channel, and staple follower 50 urges the entire staple stack in the distal direction in response to the force applied by spring 52. The distal-most staple in the stack bears against the distal end portion of pusher guide plate 60.

Channel 70 is provided between an upper surface of central body part 22 and pusher guide plate 60. Channel 70 is longitudinally curved to form an arc of a circle. Circular arcuate staple pusher 80 is mounted for arcuate reciprocation in channel 70. As in stapler 10, staple pusher 80 in stapler 110 is substantially rigid or inflexible. The proximal end portion of staple pusher 80 is attached to trigger 120 by means of reciprocal pusher actuator member 124. Accordingly, when trigger 120 is pivoted counter-clockwise about pivotal axis 122 as viewed in FIGS. 17 and 18, staple pusher 80 translates in the distal direction along channel 70. Staple pusher 80 is resiliently biased in the proximal direction by compression coil spring 126 which extends between central body part 22 and pusher actuator member 124. Spring 126 also resiliently biases trigger 120 to rotate in the clockwise direction as viewed in FIGS. 17 and 18.

Figure 18:
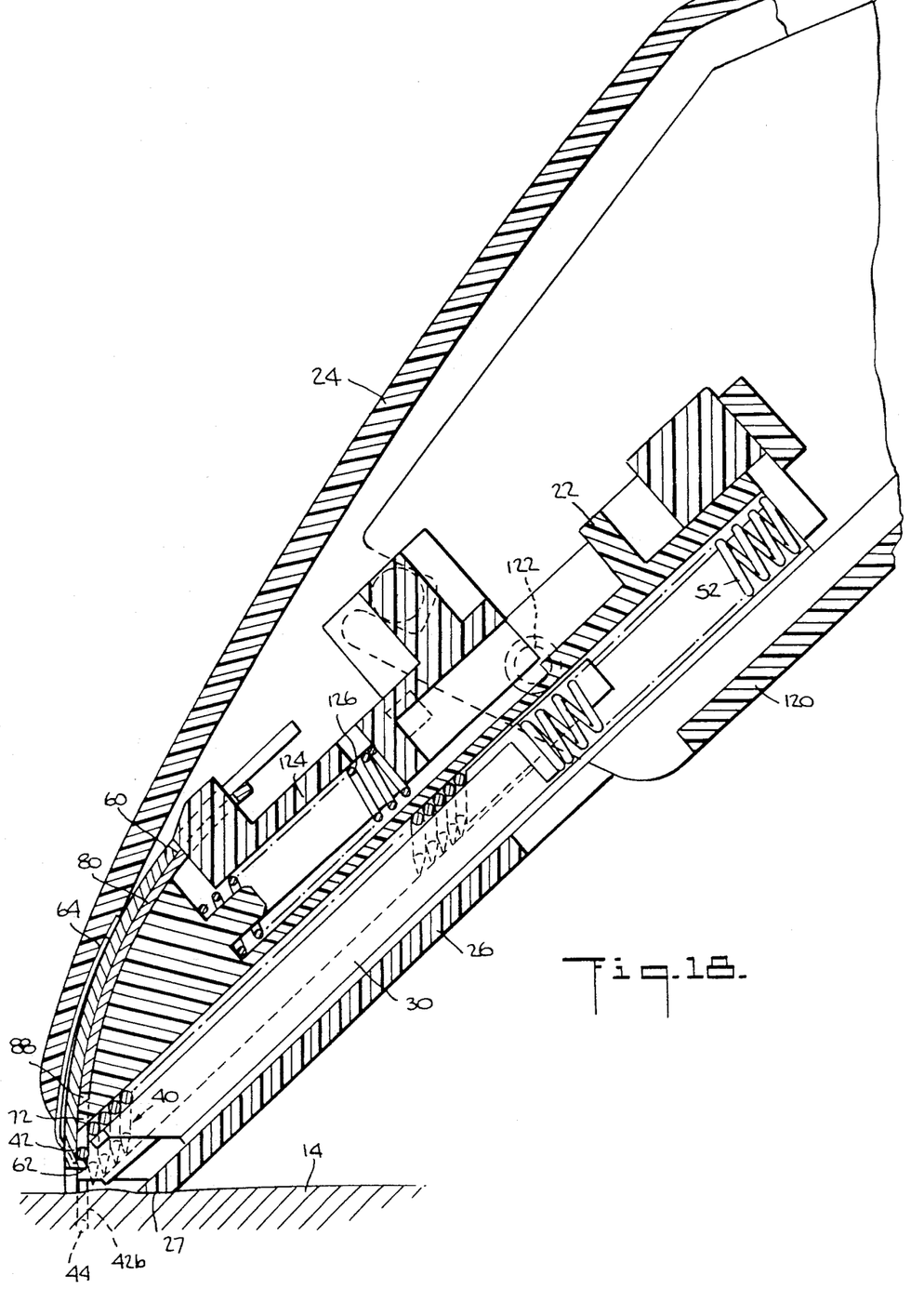
FIG. 18 is a view similar to FIG. 17 showing an intermediate stage in the operating cycle of the apparatus.
Figure 19:
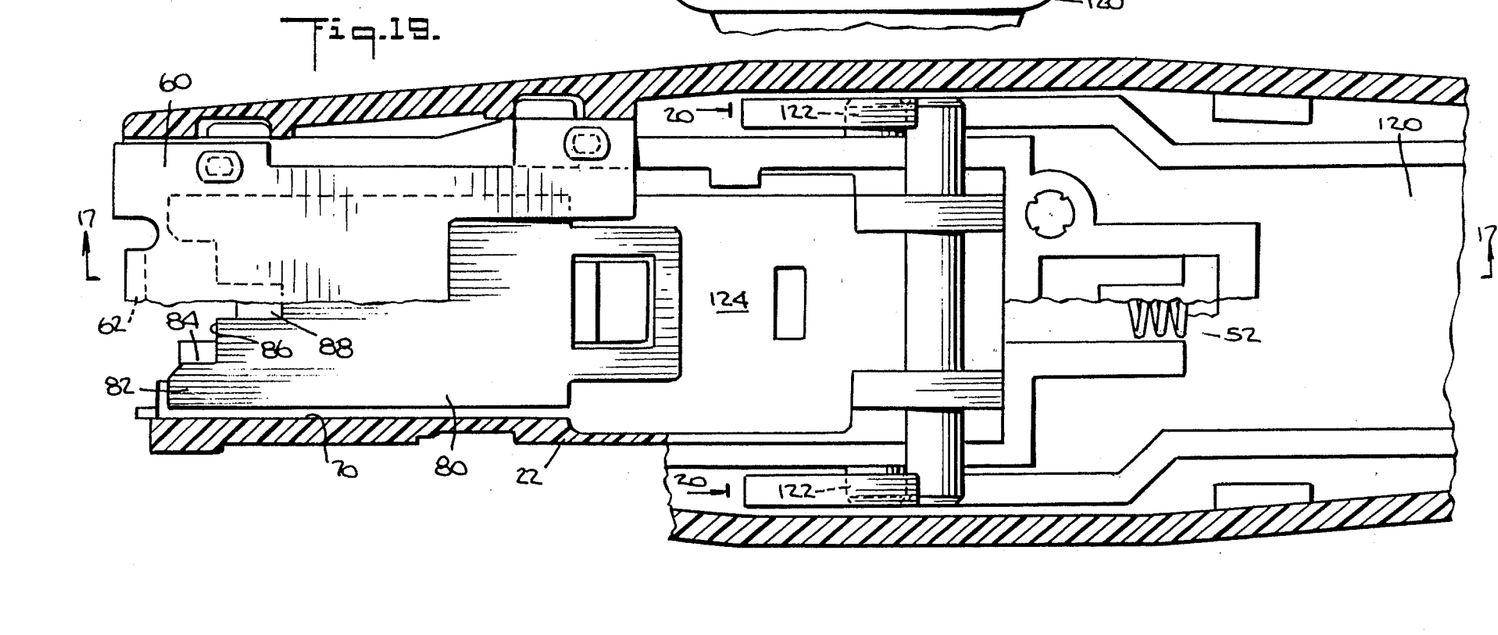
FIG. 19 is a sectional plan view of the distal portion of the apparatus of FIGS. 16-18.
Figure 20:
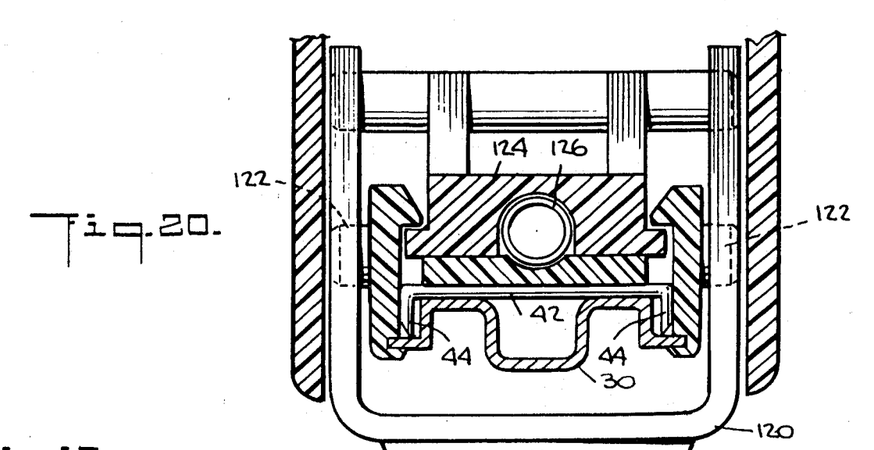
FIG. 20 is a sectional view taken along the line 20—20 in FIG. 19.

In use, the proximal portion 130 of the body of stapler 110 is held in the operator's hand with one or more fingers of that hand extended around trigger 120. Distal surface portion 27 is placed substantially parallel to or flush with the surface of the tissue 14 to be stapled, with each of the two legs of the distal-most staple being located on a respective opposite side of the wound to be closed. Trigger 120 is then squeezed toward body 20. The resulting counter-clockwise rotation of trigger 120 causes staple pusher 80 to translate arcuately in the distal direction along curved channel 70. The distal end portion of staple pusher 80 engages the distal-most staple in the staple stack and forms that staple around anvil 62 in the same way that the staple is formed in stapler 10. The staple is therefore applied to the tissue exactly as shown and described above in relation to stapler 10.

When trigger 120 is released, spring 126 restores trigger 120 and staple pusher 80 to their initial positions. Staple ejection springs 64 urge the formed staple off anvil 62 to facilitate removal of the instrument from the staple. If for any reason the formed staple does not immediately release from staple pusher 80, backstop 72 prevents the staple from being pulled back into the apparatus. As staple pusher 80 retracts past the end of the staple stack, the stack is urged in the distal direction by spring 52 and staple follower 50 so that the next staple in the stack moves into position for contact by staple pusher 80 when the apparatus is operated again.

It will be understood that the foregoing is only illustrative of the principles of the invention, and that various modifications can be made by those skilled in the art without departing from the scope and spirit of the invention. For example, as illustrated by the ring handle and trigger actuators described above, various types and shapes of actuator elements can be employed to satisfy the preferences of various operators or to meet the requirements of various applications of the apparatus.

We claim:
1. A surgical stapler comprising:
   a longitudinal body adapted to be held with the longitudinal axis of the body at an acute angle to the surface of the tissue to be stapled;
   a plurality of identical surgical staples disposed in the body in a stack having a longitudinal axis substantially parallel to the longitudinal axis of the body, each staple having a longitudinal crown and two substantially parallel legs substantially perpendicular to the crown at respective opposite ends of the crown so that the crown and legs of each staple define a plane, the plane of each staple being substantially perpendicular to the surface of the tissue to be stapled when the body is held at said acute angle to the surface of the tissue;
   an anvil adjacent a central portion of the crown of the distal-most staple in the stack, the crown of said staple also including an end portion adjacent each end of the central portion;
   a substantially inflexible, longitudinally circular arcuate staple pusher mounted for arcuate reciprocation relative to the body, the proximal end portion of the staple pusher being substantially parallel to but spaced from a proximal portion of the stack, and the plane of the distal-most staple in the stack being substantially tangent to the distal end portion of the staple pusher, the distal end portion of the staple pusher including (a) two laterally spaced, distally extending fingers, each of which engages a respective one of the end portions of the crown of the distal-most staple, and (b) a longitudinal slot between the fingers for allowing the central portion of the crown of the distal-most staple and the anvil to enter the slot when the crown of the distal-most staple is bent around the anvil; and
   means for arcuately reciprocating the staple pusher toward the distal-most staple in the stack so that the fingers bend the end portions of the crown of the distal-most staple around the anvil.
2. The apparatus defined in claim 1 further comprising means for resiliently urging the stack of staples in the distal direction.

3. The apparatus defined in claim 2 further comprising means for resiliently urging the staple pusher in the arcuately proximal direction.

4. The apparatus defined in claim 3 wherein the means for reciprocating the staple pusher comprises a pair of ring handles mounted for pivotal motion in a plane substantially perpendicular to a plane perpendicular to the longitudinal axis of the stack of staples.

5. The apparatus defined in claim 4 further comprising means for resiliently urging the rings of the ring handles apart.

6. The apparatus defined in claim 3 wherein the means for reciprocating the staple pusher comprises a trigger mounted for pivotal motion about an axis substantially parallel to a plane perpendicular to the longitudinal axis of the stack of staples.

7. The apparatus defined in claim 6 further comprising means for resiliently urging the trigger in the direction opposite the direction in which it must be pivoted to reciprocate the staple pusher in the arcuately distal direction.

8. The apparatus defined in claim 3 further comprising a fixed staple stop transverse to the staple pusher at a location proximal of the central portion of the crown of the distal-most staple for substantially preventing the crown of a staple which has been bent around the anvil from being pulled back past the staple stop when the staple pusher is arcuately reciprocated away from the anvil, and wherein the slot in the distal end of the staple pusher allows the fingers at the distal end of the staple pusher to pass the staple stop and to operate on the crown of the distal-most staple.

9. The apparatus defined in claim 8 wherein the dimension of the anvil parallel to the crown of the distal-most staple is substantially greater than the parallel dimension of the staple stop, and wherein the slot has a distal portion which is wider than said dimension of the anvil, and a proximal portion which is narrower than said dimension of the anvil but wider than said dimension of the staple stop.

10. The apparatus defined in claim 3 wherein the staple pusher reciprocates in a longitudinally curved channel having substantially the same curvature as the staple pusher, and wherein the side of the distal end portion of the curved channel adjacent the convex side of the staple pusher is adjacent the distal end of the staple stack so that the distal-most staple bears against said side of the distal end portion of the curved channel prior to being bent around the anvil.

11. The apparatus defined in claim 10 wherein the anvil is cantilevered from said side of the distal end portion of the curved channel.

12. The apparatus defined in claim 11 wherein the distal end of the curved channel communicates with the exterior of the body, and wherein the exterior surface of the body surrounding the distal end of the curved channel defines a plane substantially perpendicular to the longitudinal axis of the distal end portion of the curved channel.

13. The apparatus defined in claim 3 wherein said acute angle is in the range from 30° to 60°.

14. The apparatus defined in claim 13 wherein said acute angle is approximately 45°.

* * * * *

UNITED STATES PATENT AND TRADEMARK OFFICE
CERTIFICATE OF CORRECTION

PATENT NO. : 4,410,125

DATED : October 18, 1983

INVENTOR(S) : Douglas G. Noiles and David T. Green

Figure 6:
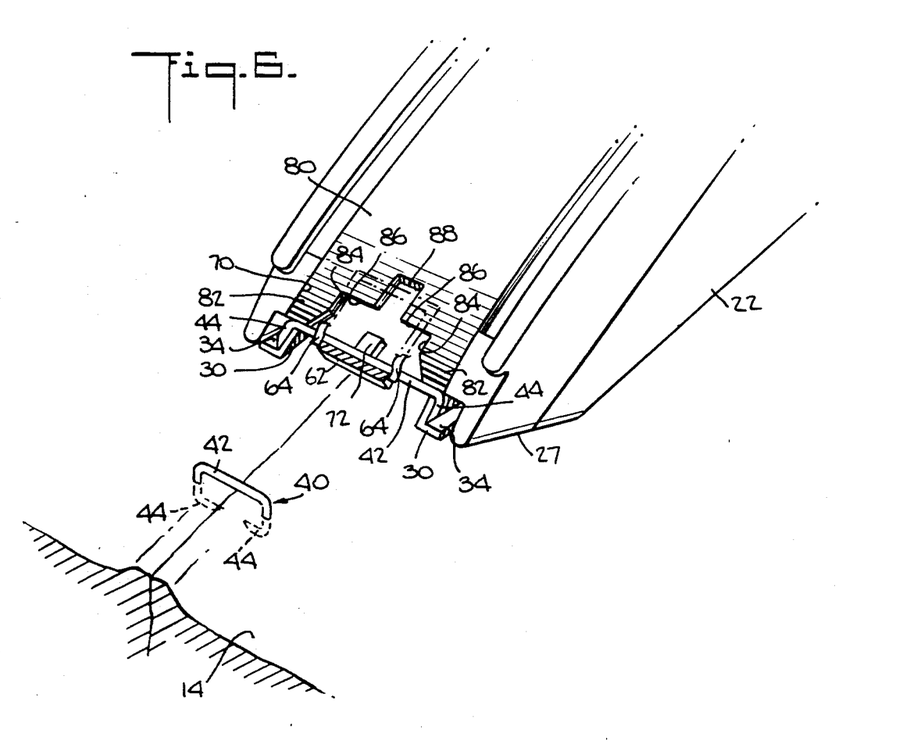
FIG. 6 is an enlarged perspective view of the top of the distal portion of the apparatus of FIGS. 1-5 with the top cover removed and showing the apparatus prior to commencement of an operating cycle.

It is certified that error appears in the above—identified patent and that said Letters Patent is hereby corrected as shown below:

| Column | Line | |
|---|---|---|
| 2 | 68 | "Fig. 6" should be --Fig. 16-- |
| 6 | 32 | "track" should be --stack-- |

Signed and Sealed this

Twenty-fourth Day of April 1984

[SEAL]

Attest:

GERALD J. MOSSINGHOFF

*Attesting Officer*  *Commissioner of Patents and Trademarks*